(12) United States Patent
LaFontaine et al.

(10) Patent No.: US 6,923,805 B1
(45) Date of Patent: *Aug. 2, 2005

(54) ELECTROPHYSIOLOGY ENERGY TREATMENT DEVICES AND METHODS OF USE

(75) Inventors: Daniel M. LaFontaine, Plymouth, MN (US); Jenifer Kennedy, Minneapolis, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/713,749

(22) Filed: Nov. 14, 2000

Related U.S. Application Data

(63) Continuation of application No. 09/248,171, filed on Feb. 9, 1999, now Pat. No. 6,168,594, which is a continuation of application No. 08/746,662, filed on Nov. 14, 1996, now Pat. No. 5,902,328, which is a continuation of application No. 08/212,297, filed on Mar. 11, 1994, now Pat. No. 5,584,872, which is a continuation of application No. 07/976,406, filed on Nov. 13, 1992, now abandoned.

(51) Int. Cl.$^7$ .............................................. A61B 18/18

(52) U.S. Cl. ............................ 606/41; 606/32; 606/48; 607/96; 607/101; 604/916

(58) Field of Search ........................ 606/41, 10, 13–16, 606/32–52; 607/113, 88, 89, 92, 93, 96–105; 604/915–921

(56) References Cited

U.S. PATENT DOCUMENTS

| 623,022 A | 4/1899 | Johnson |
| 2,043,083 A | 6/1936 | Wappler |
| 3,473,087 A | 10/1969 | Slade |
| 3,543,760 A | 12/1970 | Bolduc |
| 3,642,008 A | 2/1972 | Bolguc |
| 3,659,588 A | 5/1972 | Kahn et al. |
| 3,680,544 A | 8/1972 | Shinnink et al. |
| 3,720,209 A | 3/1973 | Bolduc |
| 3,807,391 A | 4/1974 | Bolduc |

(Continued)

FOREIGN PATENT DOCUMENTS

DE   OS 2124684   11/1972

(Continued)

*Primary Examiner*—A. Farah
(74) *Attorney, Agent, or Firm*—Bingham McCutchen LLP

(57) ABSTRACT

Apparatus and methods are provided for ablating body tissue using radio frequency (RF) energy. A catheter having a lumen for delivering fluid can be inserted into a patient's body. A porous member, which may be expandable, is attached to the distal portion of the catheter. The porous member defines an interior region in communication with the lumen, such that the interior region is capable of receiving electrolyte fluid delivered from the proximal portion of the catheter. An RF electrode is disposed in the interior region and is configured for coupling to a source of RF energy, whereby RF energy may be transferred from the electrode to selected tissue areas in a patient's body via electrolyte fluid delivered through the lumen and into the interior region of the porous member.

10 Claims, 3 Drawing Sheets

U.S. PATENT DOCUMENTS

| | | | | |
|---|---|---|---|---|
| 4,058,116 | A | 11/1977 | Bucalo | |
| 4,116,198 | A | 9/1978 | Roos | |
| 4,248,231 | A | 2/1981 | Herczog et al. | |
| 4,326,529 | A | 4/1982 | Doss et al. | |
| 4,432,367 | A | 2/1984 | Piesinger | |
| 4,641,649 | A | 2/1987 | Walinsky et al. | |
| 4,644,960 | A | 2/1987 | Johans | |
| 4,674,499 | A | 6/1987 | Pao | |
| 4,699,147 | A | 10/1987 | Chilson et al. | |
| 4,785,815 | A | 11/1988 | Cohen | |
| 4,832,048 | A | 5/1989 | Cohen | |
| 4,869,248 | A | 9/1989 | Narula | |
| 4,896,671 | A | 1/1990 | Cunningham et al. | |
| 4,922,912 | A | 5/1990 | Watanabe | |
| 4,931,047 | A | 6/1990 | Broadwin et al. | |
| 4,940,064 | A | 7/1990 | Desai | |
| 4,943,290 | A * | 7/1990 | Rexroth et al. | 606/45 |
| 4,945,912 | A | 8/1990 | Langberg | |
| 4,966,597 | A | 10/1990 | Cosman | |
| 4,974,595 | A | 12/1990 | Nordenstrom | |
| 4,979,948 | A * | 12/1990 | Geddess et al. | 606/33 |
| 4,985,028 | A | 1/1991 | Isner et al. | |
| 5,047,028 | A * | 9/1991 | Qian | 606/49 |
| 5,056,517 | A | 10/1991 | Fenici | |
| 5,083,565 | A | 1/1992 | Parins | |
| 5,104,393 | A | 4/1992 | Isner et al. | |
| RE33,925 | E | 5/1992 | Bales | |
| 5,111,832 | A | 5/1992 | Saksena | |
| 5,122,138 | A | 6/1992 | Manwaring | |
| 5,167,659 | A | 12/1992 | Ohtomo et al. | |
| 5,300,069 | A | 4/1994 | Hunsberger et al. | |
| 5,460,628 | A * | 10/1995 | Neuwirth et al. | 606/27 |
| 5,472,441 | A * | 12/1995 | Edwards et al. | 128/898 |
| 5,498,238 | A * | 3/1996 | Shapland et al. | 604/103.01 |
| 5,722,403 | A * | 3/1998 | McGee et al. | 600/373 |
| 5,797,903 | A * | 8/1998 | Swanson et al. | 600/374 |

FOREIGN PATENT DOCUMENTS

| | | |
|---|---|---|
| EP | 0 223 023 | 5/1987 |
| EP | 0223023 | 5/1987 |
| GB | 1033971 | 6/1966 |

* cited by examiner

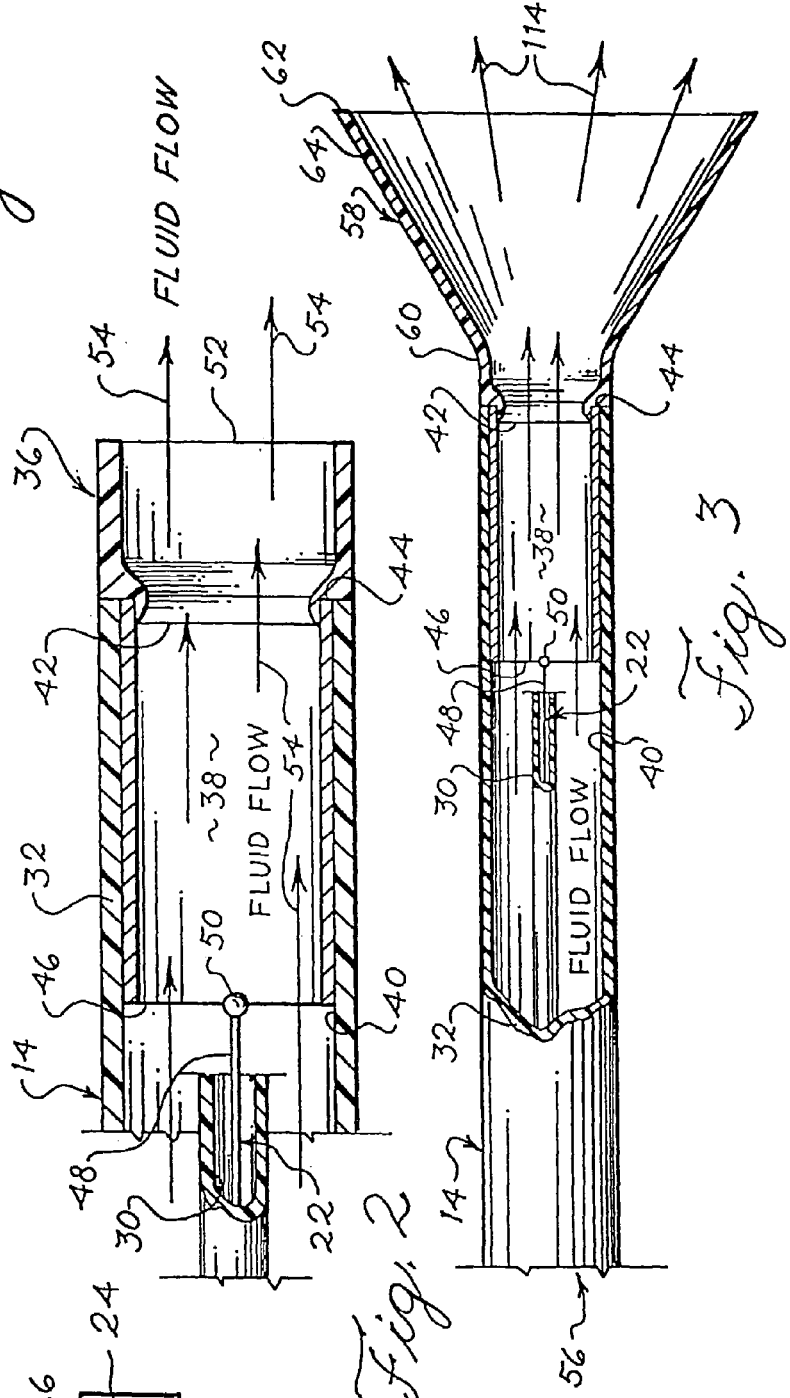

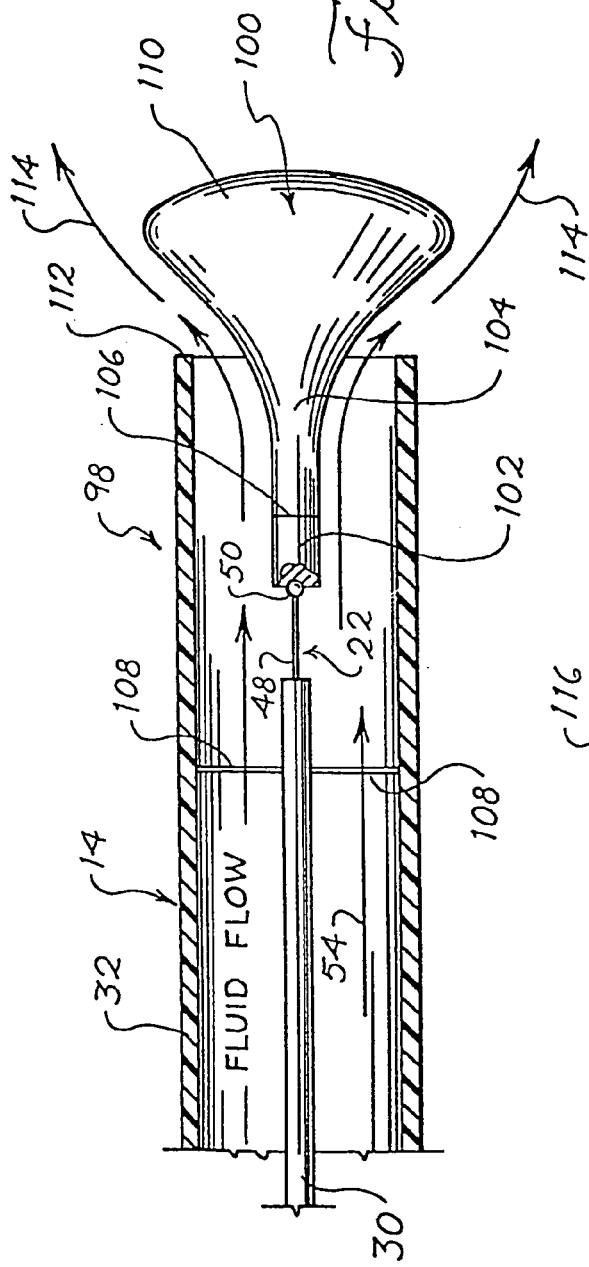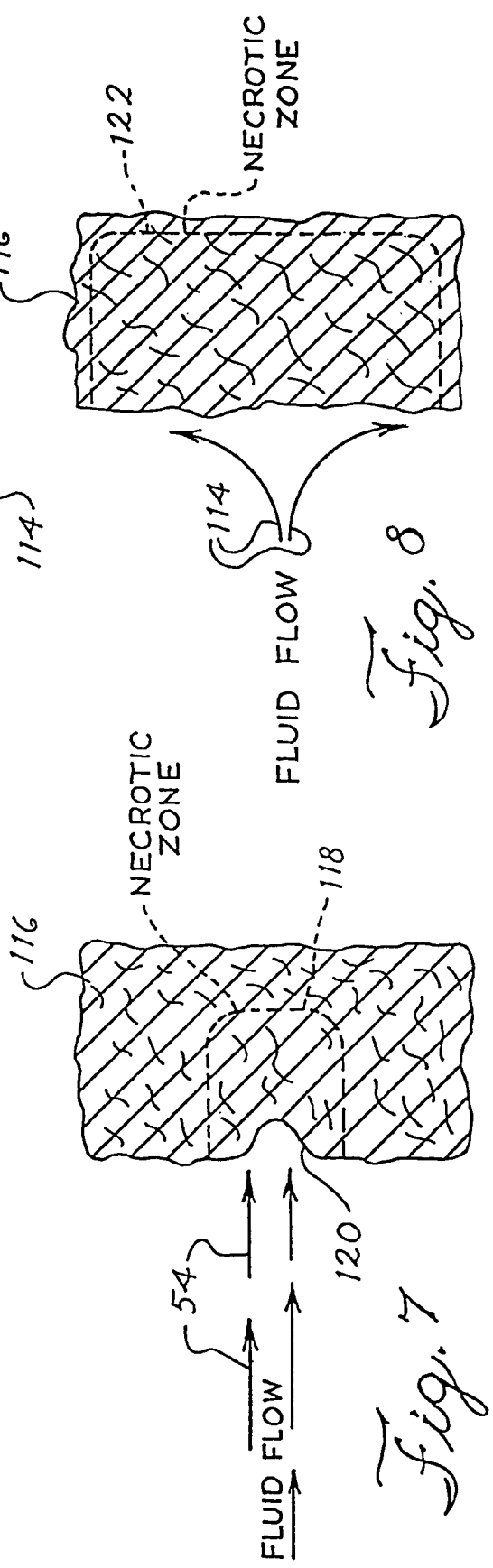

ELECTROPHYSIOLOGY ENERGY TREATMENT DEVICES AND METHODS OF USE

This a Continuation of application Ser. No. 09/248,171, filed on Feb. 9, 1999, now U.S. Pat. No. 6,168,594, which is a Continuation of application Ser. No. 08/746,662, filed on Nov. 14, 1996, now U.S. Pat. No. 5,902,328, which is a Continuation of application Ser. No. 08/212,297, filed on Mar. 11, 1994, now U.S. Pat. No. 5,584,872, which is a Continuation of application Ser. No. 07/976,406 filed on Nov. 13, 1992, now abandoned.

BACKGROUND OF THE INVENTION

The present invention relates generally to a novel device for treating tissues within a patient and to novel methods for performing such treatments. More specifically, the invention relates to a novel energy treatment device, especially an electrophysiology, RF energy thermal tissue treatment device, and to methods of using such a device to treat tissues.

The human heart is an engineering marvel which can pump blood through a patient's body for, in some cases, over one hundred years without serious difficulty or complication. The heart itself is about the size of a clenched fist, and has four chambers which receive blood from, and pump blood through the body. Basically, blood courses through a patient's vascular system, supplying necessary elements to sustain life and removing wastes, such as carbon dioxide, from the body. Once the blood has passed through the vascular system, the blood returns to the heart, where it enters a first blood receiving chamber, referred to as the right atrium. The right atrium is connected to a first blood pumping chamber, called the right ventricle, by a valve which prevents back flow of blood from the right ventricle into the right atrium when the right ventricle contracts to pump blood. The right ventricle is also connected to a pulmonary artery for delivering blood to the lungs so that the blood can basically get rid of collected carbon dioxide and replace it with oxygen. This re-oxygenates the blood, and the blood is ready to course through the patient's body again.

After the blood has been re-oxygenated, the blood returns to the heart through a blood vessel called the pulmonary vein. The end of the pulmonary vein opposite to the end connected to the lungs is connected to a second blood receiving chamber of the heart, called the left atrium. The left atrium is connected to a second blood pumping chamber, known as the left ventricle, through a valve which prevents back flow of blood from the left ventricle into the left atrium as the left ventricle contracts. The left ventricle is also connected to a blood vessel, called the aorta, which accepts blood from the left ventricle and directs that blood into the patient's vasculature. In this way, re-oxygenated blood is returned to the body, where it can supply more necessities, like oxygen, and remove more wastes, like carbon dioxide.

The structure of the heart is particularly adept at performing repeated, regular contractions of the ventricles to preserve substantially constant blood flow through the patient's body. The tissues making up the heart generally comprise a layer of muscle and cardiac cells, called the myocardium, disposed between inner and outer lining layers of the heart. The muscle cells of the myocardium respond to electrical processes, pulses or stimuli to properly contract and relax in order to pump blood. Thus, there are two electrical processes which take place during pumping of blood by the heart. The first, called depolarization, occurs when muscle cells of the myocardium are stimulated, thereby causing the myocardium to contract, which forces blood out of the ventricles. The second process is called repolarization wherein the muscle cells of the myocardium relax, thereby allowing blood to flow into the ventricles from the appropriate atrium. For these processes to occur properly, thereby insuring proper blood flow, the stimulation of the muscle cells of the myocardium must be regular. If this stimulation is not regular, then the heart may not function properly, which may compromise the patient's health. The muscle cell stimuli are often carried within the myocardium along specific, correct pathways which can provide for regular stimulation of the muscle cells. However, if these correct pathways are not followed, the stimulation of the muscle cells may become irregular.

There are at least two ways by which the stimulation of the muscle cells of the myocardium may become irregular. The first will be called the accessory pathway condition for the purposes of this disclosure; the second being called the infarct-related condition. The accessory pathway condition can be generally characterized by a condition where the electrical stimuli travel through other, accessory stimuli pathways, in addition to the proper pathways. These other, accessory pathways which are formed on the heart result in irregular stimulation of the muscle cells. The accessory pathway condition often exists at birth, and may be caused by a malformation of the heart. This condition, although it exists at birth, may not show up in a relatively young heart. This condition may worsen over time and lead to irregular stimulation of the muscle cells and irregular pumping of blood.

One method of treating the accessory pathway condition is by electrophysiology ablation of portions of the heart. This treatment method takes advantage of the fact that the correct pathways of muscle cell stimulation, as well as the accessory pathways exist within the heart. If the accessory pathways are effectively eliminated, then muscle cell stimulation will take place only along the correct pathways discussed earlier, thereby leading to a substantially regular heart beat. In order to effectively eliminate the accessory pathways, an electro-ablation or mapping catheter is used to apply radio frequency (hereinafter "RF") electrical energy to the accessory pathways.

Specifically, a mapping catheter, well known to those having ordinary skill in the relevant art, is placed within the heart to map the heart and locate the accessory pathways in known fashion. Once the accessory pathways are located, the distal end of the mapping catheter is placed adjacent a location of an accessory pathway in the heart. The mapping catheter may have a suitable conductor, such as an electrode, or other suitable RF energy transmission device, located on the distal end of the catheter for supplying RF energy to the heart. RF energy is supplied to the relevant portions of the heart to disrupt stimuli transmission along the accessory pathway. Specifically, sufficient RF energy is applied to the heart to heat, and thereby ablate, that portion of the heart. Ablation of the portion of the heart changes that portion into scar tissue. Since scar tissue does not conduct muscle cell stimuli as readily as healthy portions of the heart, the accessory pathways are effectively eliminated.

In order to perform effective elimination of the accessory pathways by delivery of RF energy, the distal tip of the mapping catheter, and specifically the electrode, must be physically engaged against the portion of the heart associated with the accessory pathway. This is necessary to insure proper energy transmission to the pathway to be eliminated. This physical engagement must be maintained throughout the treatment. Maintaining the physical engagement may be difficult, especially upon consideration that the heart is continuously moving as it beats. In addition, the RF energy present in the distal tip conductor can dehydrate or otherwise effect blood adjacent the conductor. Thus, blood can coagulate around the conductor forming blood clots or coagulum. Because clotted blood does not conduct electrical energy well, the blood clots on the conductor can electrically insulate the conductor, thereby further limiting the efficiency of RF energy transmission to the relevant portions of the heart. If sufficient blood clot material forms on the conductor, the entire mapping catheter may have to be removed from the patient and cleaned. Once cleaned, the mapping catheter will have to be reinserted into the patient's heart to complete the treatment. This procedure of catheter removal, cleaning, and reinsertion may take considerable time, on the order of one half of one hour or so, which may not be beneficial to the patient. In addition, thermal energy may be generated in the distal tip conductor, thereby further reducing the efficiency of RF energy transmission to the heart tissue. Specifically, the thermal energy may dry out or desiccate adjacent blood and tissues, thereby creating a high impedance at the conductive interface between the tissues to be treated and the conductor. The high impedance may reduce the flow of current to the tissues and the amount of energy that can be delivered thereto. Thus, the depth of energy penetration into the tissues may be correspondingly limited.

Similar occurrences can be encountered with the infarct-related condition causing irregular transmission of muscle cell stimuli. Myocardial infarction is the technical term for the destruction or death of cells which make up the myocardium by events such as a heart attack. The infarct-related condition is characterized by certain cells in the myocardium being damaged such that they do not conduct muscle cell stimuli properly. Specifically, the damaged cells may not contract in response to stimuli in a regular fashion, thereby forming what is referred to as a re-entrant circuit in the heart. This too can cause irregular heart function.

The infarct-related condition is treated in substantially the same manner as described above. A mapping catheter is inserted into the patient's heart to locate the sites of re-entrant circuits. Once these sites are found, the conductor on the distal tip of the mapping catheter is physically engaged against the identified portions of the heart to supply RF energy to the site. The site is heated by the RF energy sufficiently to effectively eliminate the re-entrant circuit, thereby restoring substantially normal heart function. This treatment method, however, is also subject to the same concerns discussed earlier with respect to maintaining the physical engagement of the electrode and the heart, blood clotting, and tissue desiccation effects.

The above-discussed RF ablation treatment techniques and devices can comprise an effective treatment means for certain defects in heart functionality. However, these techniques and devices do have the disadvantages described above which may make their performance suboptimal in certain situations. Accordingly, it is desirable to provide an improved method and device for performing RF ablation treatment of tissues within a patient's body which are not subject to the concerns discussed in detail in the preceding paragraphs. The present invention is intended to provide such an improvement.

Specifically, the present invention provides improved, novel devices and methods for performing energy treatment, and specifically electrophysiology RF energy treatment of tissues within a patient's body. Preferably, the novel devices and methods will not be as subject to the concerns regarding physical engagement maintenance and blood coagulating or clotting on a conductor as are some similar devices and methods of the prior art. The novel devices and methods may be applicable in subjecting to RF energy, and the like, tissues located in various portions, such as a coronary portion or a peripheral portion, of a patient's body.

SUMMARY OF THE INVENTION

A general object of the present invention is to provide a novel device and method for performing energy treatment of tissues within a human body.

A more specific object of the invention is to provide a novel electrophysiology energy treatment device and method, and especially an RF electrophysiology tissue treatment device and method.

An additional object of the present invention is to provide a novel energy treatment device which is easier to maintain in operative, treating contact with tissues to be treated, such as tissues of a beating heart, and the like, than some prior art devices.

A novel electrophysiology device, constructed according to the teachings of the present invention, for treating tissues within a patient with electrical energy comprises an elongate catheter tube having a distal end insertable into a patient. An electrode is within the catheter tube adjacent the distal end and locatable within the patient's body, and an electrolyte fluid flows within the catheter tube for electrically connecting the electrode to the tissues to be treated within the patient's body.

Novel methods, according to the teachings of the present invention, for treating tissues within a patient by electrical energy are also provided. One such method comprises the steps of: providing an energy treatment device having an electrode and a distal tip, the electrode being located within the patient's body; placing the distal tip within the patient's body adjacent the tissues to be treated with electrical energy; energizing the electrode with electrical energy; and electrically connecting the electrode to the tissues to be treated with an electrolyte fluid flowing from the electrode to the tissues for treating the tissues with electrical energy.

BRIEF DESCRIPTION OF THE DRAWINGS

The organization and manner of the structure and operation of the invention, together with further objects and advantages thereof, may best be understood by reference to the following description taken in connection with the accompanying drawings, wherein like reference numerals identify like elements in which:

FIG. 1 is a fractured elevational view of an electrophysiology energy treatment device, constructed according to the teachings of the present invention, a distal portion of which is enlarged for clarity;

FIG. 2 is an enlarged sectional view of a distal portion of the electrophysiology energy treatment device of FIG. 1;

FIG. 3 is a view, similar to that of FIG. 2, of an alternative embodiment of the invention;

FIG. 6 is a view, similar to that of FIG. 3, of another embodiment of the invention;

FIG. 7 is a somewhat schematic representation of a zone of necrotic cells formed on a tissue by a relatively concentrated flow of energy-bearing electrolyte fluid; and FIG. 8 is a view, similar to that of FIG. 7, of a zone of necrotic cells formed on a tissue by a relatively divergent flow of energy-bearing electrolyte fluid.

DETAILED DESCRIPTION OF THE PREFERRED EMBODIMENTS

Figure 4:
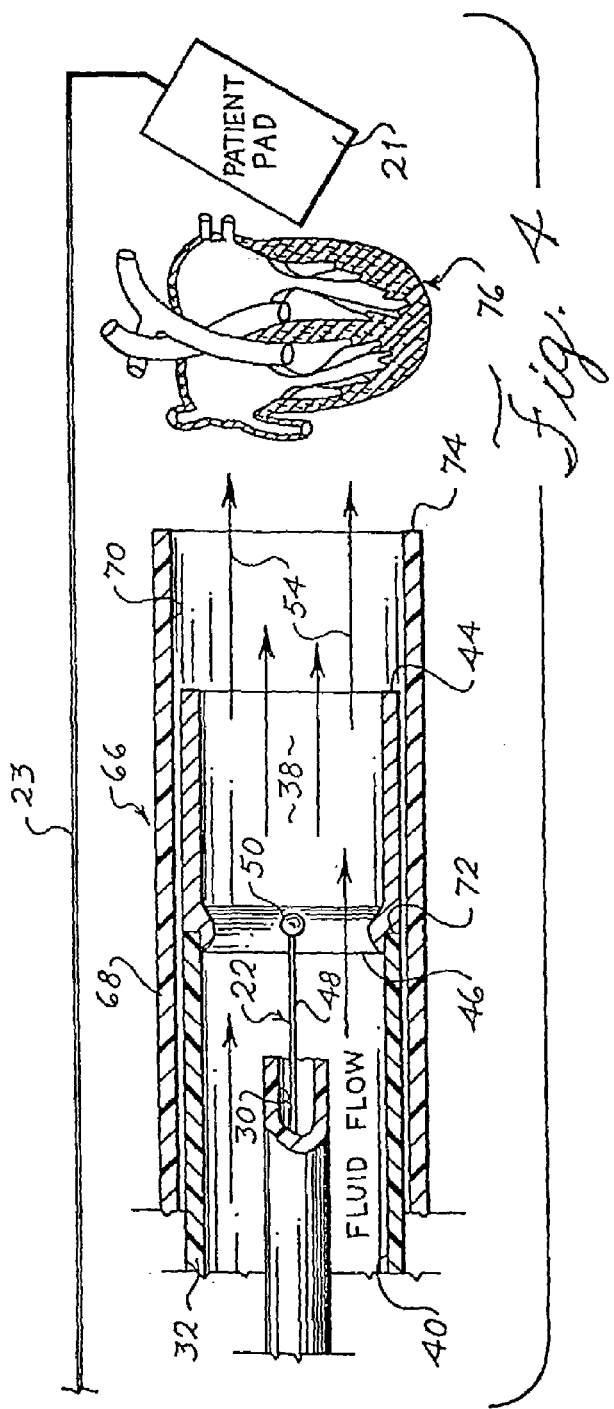
FIG. 4 is an enlarged, partially sectioned side elevational view of a distal portion of another embodiment of the invention, showing somewhat schematically a portion of an electrical circuit formed thereby.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

Referring initially to FIG. 1, a novel electrophysiology energy treatment device 10, constructed according to the teachings of the present invention, for treating tissues inside a patient's body with electrical energy, specifically RF energy, is shown. For the sake of clarity, the energy treatment device 10 will be discussed with respect to its employment in treating heart tissue, but it is to be clearly understood that the scope of the present invention is not to be limited to that employment. It is envisioned that the teachings and embodiments of this invention may have utility with treating a plurality of tissues in a plurality of ways. For example, the embodiments and methods of the present invention may be applicable to tissues located in a patient's peripheral vasculature. In addition, while the embodiments of the invention are discussed herein with respect to energy treatment of tissues, it is to be understood that the embodiments can also be used to sense electrical pulses within tissues, i.e. like a mapping catheter.

The general construction of the energy treatment device 10 is illustrated in FIG. 1. Specifically, the energy treatment device 10 comprises a manifold assembly 12 and a tube assembly 14 insertable intravascularly into a patient. The manifold assembly 12 has a substantially Y-shaped configuration having at least two proximal ports 16A and 16B, and at least one distal port 18, to which a proximal end of the tube assembly 14 is attached. The proximal port 16A is operatively connected to a suitable source 20 of RF energy by a length of wire 22 for delivering RF energy from the energy source 20 to the manifold assembly 12.

The energy source 20 is preferably a unit available from Radionics of Burlington, Mass., and specifically is a unit which Radionics designates by model number CBC1. Of course, equivalent units can also be used without departing from the scope of the invention. In a presently contemplated mode of operation of the energy treatment device 10, the energy source 20 delivers approximately 50 Watts of power into 100 Ohms at about 70 Volts (root mean square value). This power is delivered substantially in the form of a sine wave at a frequency of about 500,000 Hertz (Hz). The energy source 20 is also preferably comprised of a unipolar energy system, and is also connected, by means of a wire 23, to an electrically conductive patient pad 21, well known in the relevant art, which can be placed upon the patient's skin adjacent the tissues to be treated for completing an electrical circuit, thereby allowing RF energy to flow through the tissues to be treated. It is to be understood that the patient pad 21 can be replaced by a conductive veinous catheter or a conductive needle inserted into the patient without departing from the scope of the present invention. In this manner, the energy system can be bi-polar.

The wire 22 carrying the RF energy from the energy source 20 to the manifold assembly 12 extends through the proximal port 16A, the manifold assembly 12, and the distal port 18 and enters the tube assembly 14, as will be discussed in greater detail later. The proximal port 16A has suitable sealing means engageable with the wire 22 for insuring that fluid disposed within the manifold assembly 12 will not leak out of the manifold assembly 12 through the proximal port 16A around the wire 22. In an exemplary embodiment of the energy treatment device 10, the wire 22 is a 26 gauge silver stranded wire having an insulating layer, composed of TEFLON®, disposed on the outer diameter surface of the silver strands.

The proximal port 16B is operatively connected to a source of fluid 24 by a suitable conduit 26 for delivering fluid from the fluid source 24 to the manifold assembly 12. The fluid provided by the fluid source 24 is preferably an electrolytic solution of an ionic salt, such as saline solution, contrast media, solutions of calcium or potassium salts, solutions of radio-nuclides, and the like, and serves as a novel means for delivering RF energy from the wire 22 to the tissue to be treated by the energy treatment device 10, as will be discussed below. The electrolyte fluid preferably has a relatively low impedance with respect to the tissues to be treated, and thus, a small amount of fluid is required to deliver the desired amount of RF energy to the patient's tissues. In a currently contemplated embodiment of the energy treatment device, the electrolyte fluid comprises a solution of 35 grams of sodium chloride in 100 ml of water. The electrolyte fluid may be of any suitable consistency, and may be a conductive gel, similar to the 20% hypertonic saline gel sold under the name of HYPERGEL by Scott Healthcare, a unit of Scott Paper Company of Philadelphia, Pa. It is envisioned that the electrolyte fluid may also be provided as an electrolytic column which dissolves during use.

A suitable fluid pump 28, such as a syringe, a motor driven pump and the like, is provided on the conduit 26 between the fluid source 24 and the proximal port 16B for insuring flow of fluid from the fluid source 24 to the manifold assembly 12 during operation of the energy treatment device 10. The fluid pump 28 is preferably variably controllable such that the rate of fluid flow into the manifold assembly 12 and the tube assembly 14 can be varied for allowing a treating physician to alter the rate of RF energy delivery to the patient's tissues, as well as the area on the patient's tissues which are to be subjected to the delivered RF energy.

The electrolyte fluid enters the manifold assembly 12 through the proximal port 16B, which includes suitable sealing means so that no fluid leaks from the manifold assembly 12 through the proximal port 16B, and fills the interior of the manifold assembly 12. The wire 22 extending through the manifold assembly 12 is surrounded by a wire lumen 30 extending from the proximal port 16A to the distal port 18 so that RF energy on the wire 22 will not be passed to the electrolyte fluid within the manifold assembly 12.

RF energy is not delivered to the fluid within the manifold assembly 12. The manifold assembly 12 is often located a relatively significant distance from the patient's tissues to be treated with RF energy. Thus, electrical resistance to the flow of RF energy is minimized because the RF energy does not have to travel through a relatively large amount of fluid before reaching the tissues to be treated. Instead, RF energy is transmitted within the tube assembly 14 towards the tissues to be treated by the wire 22, which offers significantly less electrical resistance to RF energy transmission than a corresponding amount of fluid. This allows for increased efficiency in delivering RF energy to tissues within a patient, and also for more effective treatment of those tissues. It is believed that this efficiency may not be obtainable with an ablation or tissue treatment device having a proximally located electrode because the amount of electrolyte fluid extending between the electrode and the tissues being treated would offer sufficient resistance for reducing the efficiency of the device.

The tube assembly 14 generally includes an elongate catheter tube 32 having a proximal portion 34 and a distal tip 36 and an electrode 38. The catheter tube 32 preferably has an outer diameter of about 8 French, and has an axial length sufficient to extend from the distal port 18 on the manifold assembly 12 through the patient's vasculature to the tissues to be treated. Because the tissues to be treated may be located in various parts of the patient's body, the axial length of the catheter tube 32 can be predetermined for a given application. The catheter tube 32 defines an outer diameter having a length small enough to pass through the smallest vascular lumen through which the catheter tube 32 must pass in order to reach the desired tissues. In an exemplary embodiment of the energy treatment device 10, the catheter tube 32 comprises a stainless steel woven braid encased within a shell composed of PEBAX, which is a soft polymeric material available from. ATOCHEM (France).

The proximal portion 34 of the catheter tube 32 is attached to the distal port 18 of the manifold assembly 12 so that fluid within the manifold assembly 12 can flow into the axial length of the catheter tube 32. The connection between the proximal portion 34 of the catheter tube 32 and the distal port 18 of the manifold assembly 12 is sufficiently fluid tight so that no fluid leaks from the manifold assembly 12 or the catheter tube 32 at the juncture between the distal port 18 and the proximal portion 34 of the catheter tube 32. The juncture between the distal port 18 and the proximal portion 34 allows for fluid flow into the catheter tube 32 and also for passage of the wire lumen 30 from the manifold assembly 12 to the catheter tube 32.

The wire 22 and the wire lumen 30 extend coaxially within a fluid lumen 40 within the catheter tube 32 substantially along the entire length of the catheter tube 32, however, the wire 22 and the wire lumen 30 terminate short of the distal tip 36, as shown in FIGS. 1 through 3. The distal tip 36 of the catheter tube 32 is comprised of a rather soft, pliable polymeric material and the like, with a preferred material being PEBAX, for cushioning engagement between the entering, distal tip 36 of the energy treatment device 10 and the patient's vasculature or other tissues, and preferably has an axial length measuring substantially within the range of 0.08" to 0.5".

The electrode 38 is located within the fluid lumen 40 adjacent a proximal end 42 of the distal tip 36. In the illustrated embodiment, the electrode 38 is substantially cylindrical in configuration, and is formed from a suitable electrically conductive material, with the current embodiment of the energy treatment device 10 having an electrode 38 comprised of a silver—silver chloride material, so that electrolyte fluid passing through the fluid lumen 40 adjacent the electrode 38 can accept RF energy from the electrode 38. The electrode 38, can define other configurations without departing from the scope of the invention. In the illustrated embodiment, the electrode 38 has an axial length of about 0.15" and a diameter of less than about 8 French. Because, in a preferred embodiment, the distal tip 36 has an axial length substantially within the range of 0.08" to 0.5", a distal end 44 of the electrode 38 is offset from an open end 52 of the distal tip 36 by the same distance.

The distal end 44 of the electrode 38 is overlapped by the proximal end 42 of the distal tip 36 for insuring a firm connection among the catheter tube 32, the distal tip 36 and the electrode 38. A proximal end 46 of the electrode 38 is connected to a distal end 48 of the wire 22 by a bead 50 formed by a welding, brazing or other suitable process. The wire lumen 30 terminates proximally of the proximal end 46 of the electrode 38 in appropriate fashion to allow the distal end 48 of the wire 22 to be electrically connected to the electrode 38 for transferring RF energy on the wire 22 to the electrode 38. It is to be noted, however, that the distal, terminal end of the wire lumen 30 is substantially sealed so that electrolyte fluid within the fluid lumen 40 cannot enter the wire lumen 30.

In this manner, electrical resistance of RF energy transmission from the energy source 20 to the electrode 38 is effectively minimized. Thus, RF energy reaches the electrode 38 with less attenuation than some prior art energy treatment devices. The resistance to RF energy provided by the electrode 38 and the electrical impedance of the electrode 38 is substantially similar to the resistance and impedance of the electrolytic fluid within the fluid lumen 40 so that RF energy is relatively readily transferred from the electrode 38 to the fluid as the fluid flows over the electrode 38 without substantial generation of heat. This is a significant improvement over some of the RF ablation or tissue treatment devices of the prior art whose electrically conducting distal tip may become rather hot during operation. In addition, cooling of or lack of heat generation in the electrode 38 and the adjacent surface of the myocardium tissues being treated allows deeper penetration of electrical current into the myocardium, and thus, deeper penetration of ohmic heat into the tissues. This is another improvement over the currently available RF energy treatment devices utilized in ventricular ablation.

In addition, because the electrode 38 is recessed within the catheter tube 32, and is not located at the extreme distal end of the catheter tube, as is the case with some of the RF tissue treatment devices of the prior art, blood does not clot or coagulate on the electrode 38, as it may on some prior art tissue treatment device electrodes, as discussed hereinabove. The rate of electrolyte fluid flow through the fluid lumen 40 is regulated such that the flow of electrolyte fluid provides sufficient positive pressure within the fluid lumen 40 so that blood is prevented from flowing into the fluid lumen 40 through a distal, open end 52 of the distal tip 36, thereby further reducing the chances of blood clot or coagulum formation on the electrode 38.

The construction of the distal tip 36 illustrated in FIGS. 1 and 2 is substantially cylindrical, thereby providing for substantially concentrated, linearly directed flow of RF energy-bearing electrolyte fluid from the distal end 44 of the electrode 38 to the tissues to be treated. Thus, the area of the tissues to be treated is rather small, thereby providing for focused lesion formation on the tissues. Specifically, the electrolyte fluid has relatively low electrical resistance and impedance as compared to the like physical properties of the tissues to be treated. This impedance/resistance mismatch causes RF energy in the electrolyte fluid to be transferred to the tissues of the patient against which the fluid is directed. As the RF energy is transferred to the tissues, heat is generated in the tissues, thereby producing a lesion.

Accordingly, because the path of fluid flow, indicated by arrows 54 in FIG. 2, is positively limited by the construction of the distal tip 36, the electrolyte fluid is concentrated on a relatively small portion of the tissues to be treated, assuming, of course, that the energy treatment device 10 is held fixed with respect to the tissues being treated. Therefore, it is to be appreciated that the construction of the distal tip 36 serves as a calumniator or means for positively directing RF energy-bearing electrolyte fluid against tissues to be treated in a particular pattern, thereby treating the tissues in a correspondingly similar pattern.

The substantially cylindrical construction of the distal tip 36 concentrates electrolyte fluid, but other constructions of the distal tip are also possible. The concentration of electrolyte fluid produces a focal lesion on the tissues of the patient, which may be desirable in certain circumstances where relatively small, definite portions of the patient's tissues need treatment. It is to be noted, however, that other lesions are also producible with the energy treatment device 10. Specifically, a large area lesion, i.e. a lesion larger in area on the tissues than the focal lesion, can be produced on the tissues by moving the energy treatment device 10 with respect to the tissues during operation of the device 10. This would subject a larger area of the tissues to the heating or treating effects of the RF energy-bearing electrolyte fluid. In addition, the energy treatment device 10 can be held fixed with respect to a first portion of the tissue to be treated, and then moved with respect to a second portion of the tissue during operation of the device 10. In this manner, a focal lesion can be formed on the first portion and a large area lesion can be formed on the second portion.

Referring now to FIG. 3, another embodiment of the invention is illustrated. Specifically, an electrophysiological RF energy treatment device 56 allows a treating physician to produce large area lesions on the tissues to be treated without having to move the device 56 with respect to those tissues. The energy treatment device 56 is substantially similar to the energy treatment device 10 discussed hereinabove, hence the like reference numerals for similar structures, except for the differences to be noted herein. The energy treatment device 56 differs from the energy treatment device 10 in that the energy treatment device 56 includes a novel distal tip 58 constructed for forming large area lesions. The distal tip 58 also acts as a columnator or means for positively directing electrolyte fluid against tissues to be treated.

The distal tip 58 defines a substantially frusto-conical configuration having a small diameter portion 60 and a large diameter portion 62. The small diameter portion 60 is connected to the distal end of the catheter tube 32 and defines an inner diameter substantially equal to the inner diameter defined by the catheter tube 32. The small diameter portion 60 is connected to the large diameter portion 62 by a flared wall 64 which defines a gradually increasing inner diameter. The flared wall 64 allows RF energy-bearing electrolyte fluid to define a fluid flow path, indicated by arrows 66 in FIG. 3, wider than the fluid flow path defined by the fluid flowing through the distal tip 36. Because the fluid flow path is wider, the energy treatment device 56 is able to produce a large area lesion without having to move the energy treatment device 56 with respect to the tissues being treated.

It can be understood that the distal tip 36 or 58 of the energy treatment device 10 or 56 can act as nozzle means for positively directing RF energy-bearing fluid flow in a particular pattern. Thus, in light of this embodiment of the invention, it is to be appreciated that the configuration of the distal tip of the energy treatment device can be predetermined and produced in a variety of configurations for defining fluid flow paths which can create a desired lesion formation on the tissues being treated by RF energy. Accordingly, various modifications of this nozzle means can be utilized, such as a balloon on the distal tip of the energy treatment device which is inflatable for defining various fluid flow paths, and is deflatable for facilitating intravascular movement of the device.

The structure of the embodiments of the present invention may become more clear upon reference to the following discussion of the operation of those embodiments. It is to be noted, however, that, while the following discussion of the operation of the embodiments of the invention is limited to the employment thereof in treating tissues of the human heart, this discussion is offered for purposes of illustration only and is not intended to limit the scope of this invention. As mentioned above, the embodiments and methods of the invention can be employed in treating various tissues, located in the coronary or the periphery, for example, with RF or other energies.

If a patient has a heart condition, such as the accessory pathway condition, or the infarct-related condition discussed earlier, or the like, which can be effectively treated by RF energy treatment of appropriate heart tissues, then a treating physician may choose to utilize the RP energy treatment device 10 or 56, depending upon the type of lesion on the heart tissue that is desirable to produce. The physician begins the treatment by making a suitable access into the patient's vascular system. This access may be made in the patient's neck, or other suitable location. The distal tip 36 or 58 of the energy treatment device 10 or 56 is inserted into the patient's vasculature and navigated to the tissues to be treated with RF energy. At the same time, the patient pad 21 is applied to the outside of the patient's skin adjacent the tissues to be treated so that RF energy delivered to the patient's tissues can be conducted to the patient pad 21. Because the patient pad 21 is connected to the energy source 20 by the wire 23, an electrical circuit is formed through the patient, as will be discussed in greater detail later.

The distal tip 36 or 58 is positioned adjacent the tissues, such as those associated with accessory pathway or infarct sites, of the heart to be treated. It is to be noted that a distal surface 66 of the distal tip 36 or 58 does not have to be engaged against the heart tissues in order to perform RF tissue treatment with the embodiments of the present invention. This is a substantial improvement over the like devices of the prior art which required physical engagement of the distal tip of the device with the heart tissues and maintenance of that engagement throughout the duration of the procedure, which could become difficult upon consideration that the tissues of the heart are in continuous motion as the heart beats. Thus, the embodiments of the invention can make some RF energy treatments easier to perform than before.

The distal tip 36 or 58 is located adjacent to, and specifically offset a certain distance from the tissues to be treated with RF energy. The distal tip 36 or 58 does not have to physically engage the tissues in order to insure transfer of RF energy from the energy treatment device 10 or 56 because the electrolyte fluid exiting the device 10 or 56 through the open, distal tip 36 or 58 acts as an electrical extension of the electrode 38 located within the catheter tube 32 for transmitting RF energy from the electrode 38 to the tissues. It has been empirically determined by experiment that, under the preferred operating conditions discussed above, the distance between the distal tip 36 or 58 and the tissues to be treated is preferably less than three inches to insure effective transmission of RF energy to the tissues. However, this distance should be large enough so that the movement of the tissues responsive to beating of the heart, for example, will not electrically disconnect the electrode 38 from the tissues being treated. Of course, this distance is dependent on the type of electrolyte fluid being used, and the power level supplied by the energy source 20.

Once the distal tip 36 or 58 of the energy treatment device 10 or 56 has been located adjacent the tissues to be treated, as discussed hereinabove, the fluid pump 28 is energized, thereby forcing electrolyte fluid from the fluid source 24 through the conduit 26 and into the manifold assembly 12 through the proximal port 16B. The electrolyte fluid flows through the manifold assembly 12 and into the fluid lumen 40 in the catheter tube 32, until the fluid flows over the surface of the electrode 38.

The energy source 20 is energized so that the energy source 20 preferably produces RF energy and supplies it to the wire 22. The wire 22 extends from the energy source 20 to the electrode 38 and is electrically insulated from the electrolyte fluid within the fluid lumen 40 by the wire lumen 30. Thus, the only impediment to RF energy transmission from the energy source 20 to the electrode 38 is the electrical resistance offered by the length of wire 22 extending between the energy source 20 and the electrode 38. The electrode 38 is located within the catheter tube 32 at a position offset from the distal tip 36 or 58 sufficiently for preventing blood from contacting and clotting or coagulating on the electrode 38 and is supplied with RF energy from the energy source 20 through the wire 22. In addition, the fluid pump 28 is appropriately regulated such that the fluid pump 28 maintains a steady flow of electrolyte fluid through the fluid lumen 40 sufficient for generating a positive pressure within the fluid lumen 40 for preventing flow of blood into the fluid lumen 40 through the distal tip 36 or 58. This is a significant improvement over some of the RF energy treatment devices of the prior art which have thrombogenic distal tips, e.g. an exposed distal electrode, on which blood can clot or coagulate. To prevent blood from reaching the electrode 38 and to provide effective RF energy transmission to the tissues of the heart, it has been empirically determined that, using the preferred electrolyte fluid discussed earlier, an electrolyte fluid flow rate of about 12 cc per minute should be used.

As RF energy passes into the electrode 38, electrolyte fluid passes over the surface of the electrode 38. Because the impedance and resistance of the electrode 38 is substantially equal to that of the electrolyte fluid, the RF energy on the electrode 38 relatively freely passes into the electrolyte fluid as the fluid flows over the surface of the electrode 38. The electrolyte fluid now carries RF energy produced by the energy source 20 with it as it flows past the distal end 44 of the electrode 38 and acts as an electrical extension of the electrode 38. Because of the relatively equal resistances and impedances of the electrode 38 and the electrolyte fluid, substantially little heat is generated in the electrode 38. This is an improvement over some of the RF energy treatment devices of the prior art whose distal tips may become relatively hot during operation. Also, because of the impedance and resistance match between the electrode 38 and the electrolyte fluid, the electrolyte fluid remains relatively cool, the adjacent surface of the myocardium tissues does not become excessively heated or dried out, thus, energy transfer to the inner myocardium tissues is not limited by surface tissue heating or desiccation.

The electrolyte fluid flows through the distal tip 36 or 58 and contacts the tissues to be treated. The tissues often have relatively high impedances and resistances as compared to that of the electrolyte. RF energy flows from the electrolyte to the tissues upon operative contact between the electrolyte and the tissues. The impedance and resistance mismatch between the electrolyte fluid and the tissues to be treated causes heat to be generated in the tissues, thereby causing their ablation in some circumstances, upon conduction of RF energy from the electrolyte fluid into the tissues. Because of the impedance and resistance match between the electrolyte fluid and the electrode 38 and the similar mismatch between the electrolyte fluid and the tissues being treated, the energy treatment device 10 or 56 can function more efficiently than some prior art tissue treatment devices because substantially all of the heat generated by the device 10 or 56 is generated in the tissue, and not in the device 10 or 56.

The electrical extension of the electrode 38 formed by the electrolyte fluid can change responsive to movement of the tissues being treated for maintaining operative electrical contact between the electrode 38 and the tissues without having to move the device 10 or 56. Specifically, the path of electrolyte fluid flow is positioned with respect to the tissues being treated such that if the tissues move with respect to the energy treatment device 10 or 56, such as in response to contraction and relaxation of the muscle cells of the myocardium, the tissues are maintained within the path of electrolyte fluid flow. The length of the fluid flow path from the electrode 38 to the tissues may change, but the tissues to be treated remain within the path of electrolyte fluid flow so that RF energy is substantially continuously transmitted from the electrode 38 to the tissues of the heart during operation of the energy treatment device 10 or 56.

The electrolyte fluid delivers RF energy to relevant tissues of the heart until sufficient heat is generated within those tissues to cause the treatment or ablation thereof. Once the tissues have been treated, substantially normal heart function may be restored, as described hereinabove with respect to the accessory pathway condition and the infarct-related condition. The RF energy transmitted to the tissues of the heart travels through the patient's body towards the patient pad 21. The RF energy flows towards the patient pad 21 because the patient pad 21 offers relatively low resistance and impedance as compared to the like properites of the patient's body. After the RF energy reaches the patient pad 21, that energy can be returned to the energy source 20 through the wire 23 to complete an electrical circuit. Thus, it can be appreciated that an electrical circuit conveying RF energy is formed through a patient during utilization of the energy treatment device 10 or 56.

In order to limit the effective length of the RF energy flow path within the patient, it is desirable to locate the patient pad 21 on the outer surface of the patient's skin adjacent the internal tissues being treated by the RF energy treatment device 10 or 56. The RF energy passes from the patient's body onto the patient pad 21, through the wire 23 and back to the energy source 20 to complete the electric circuit through the patient. Thus, it can be appreciated that the energy treatment device 10 or 56 comprises a monopolar system, viz. the electrode 38 and the patient pad 21, for conducting RF energy to tissues within a patient's body to subject those tissues to RF energy treatments. This aspect of the various embodiments of the invention may be more easily understood by viewing FIG. 4.

It has been empirically determined, specifically by operating the energy treatment device 10 or 56 in bovine blood, that, after approximately three minutes of operation at 50 Watts of sine wave output from the energy source 20 at 500,000 Hertz, there was no appreciable heat build-up in the distal tip 36 or 58 of the energy treatment device 10 or 56 and blood did not clot on that tip 36 or 58. In addition, it has been determined that the energy treatment device 10 or 56, after about one minute of operation, can remove tissue, thereby penetrating into the tissue to form a crater of a depth of about one half of one inch if the energy treatment device 10 or 56 is positioned to form a focal lesion. Operation of the energy treatment device 10 or 56 for longer periods, or possibly at higher power outputs, may produce a deeper penetration into tissues, or, alternatively, a wider, large area lesion may be produced. Given these results, it can be appreciated that the embodiments of the invention provide a significant improvement over the RF tissue treatment devices of the prior art.

Another embodiment, viz. an RF energy treatment device 66 of the invention, a distal portion of which is illustrated in FIG. 4, functions and is constructed somewhat similarly to the energy treatment devices 10 and 56, hence the like reference numerals for similar structures. In addition, this embodiment of the invention may allow for utilization of existing RF energy treatment devices in a unique manner which substantially avoids the above-discussed concerns with those prior art devices.

The energy treatment device 66 comprises an outer catheter tube 68 defining a lumen 70 of sufficient dimensions for accepting the catheter tube 32, as shown in FIG. 4. The catheter tube 32 is disposed coaxially within the lumen 70 and is connected, at its proximal portion 34 to a manifold assembly 12, as shown in FIG. 1. The catheter tube 68 can be a guide catheter, or similar structure, and can be positioned adjacent the tissues prior to insertion of the catheter tube 32 into the lumen 70. The dimensions of the catheter tubes 32 and 68 can be chosen for preventing or allowing for fluid, such as contrast media, to flow therebetween.

As opposed to the energy treatment devices 10 and 56, the electrode 38 of the energy treatment device 66 is connected to a distal end 72 of the catheter tube 32, and is not offset proximally of the distal end 72 of the catheter tube 32. Thus, the electrode 38 defines a distal end of the catheter tube 32, and the wire 22 is connected to the electrode 38 by the bead 50 adjacent a juncture between the distal end 72 of the catheter tube 32 and the proximal end 46 of the electrode 38. In this manner, the distal tip of the catheter tube 32 is charged with RF energy, which might cause blood to clot thereon, as it clots onto the distal electrodes of the prior art devices, as discussed above.

However, it is to be fully understood that, because of the unique structure of the energy treatment device 66, blood does not clot on the electrode 38. Specifically, as shown in FIG. 4, the catheter tubes 32 and 68 are relatively positioned such that the distal end 44 of the electrode 38 is offset proximally of a distal end 74 of the catheter tube 68, i.e. the distal end 74 of the catheter tube 68 is positioned closer to the tissues of the heart 76 to be treated than the distal end 44 of the electrode 38. The distance between the distal end 74 of the catheter tube 68 and the distal end 44 of the electrode 38 is preferably approximately within the range of 0.08" to 0.5", which is substantially the same distance between the distal end 44 of the electrode 38 and the open end 52 of the distal tip 36. This, combined with the flow of electrolyte fluid, as discussed above, should positively prevent blood from encountering and clotting on the electrode 38. Thus, as can be appreciated, the energy treatment device 66 functions substantially similarly to the energy treatment device 10 or 56.

Figure 5:
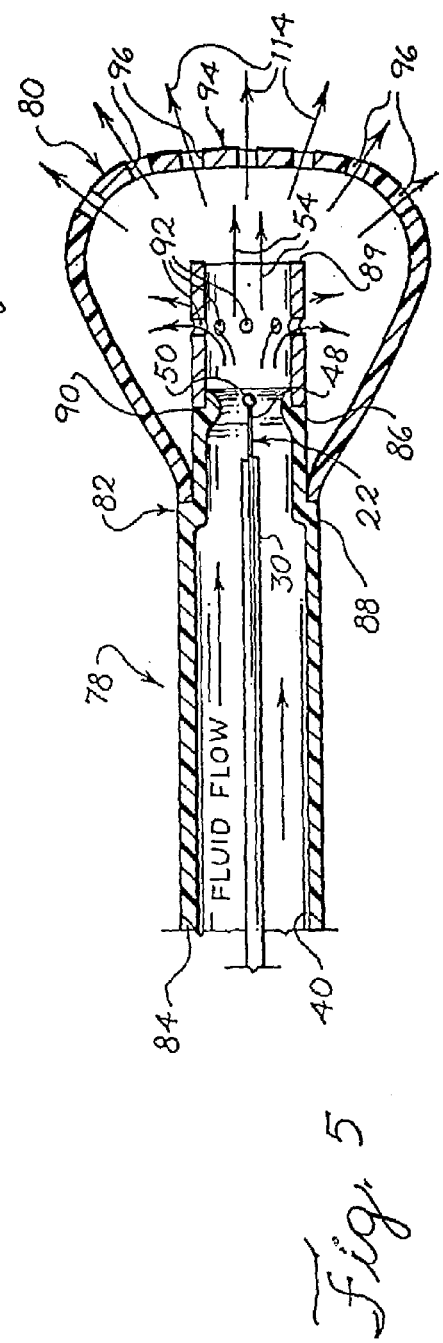
FIG. 5 is a view, similar to that of FIG. 1, of another embodiment of the invention.

Yet a further novel RF energy treatment device 78 is provided and is illustrated in FIG. 5. The energy treatment device 78 is similarly constructed to the energy treatment devices 10, 56 or 66 in some respects, hence the like reference numerals for similar structures. This energy treatment device 78 differs from the above-discussed embodiments of the invention in that the energy treatment device 78 includes a novel construction of means for positively directing electrolyte fluid flow to tissues to be treated. This novelly constructed means takes the form of an expandable member 80 disposed on a distal end 82 of a catheter tube 84, substantially similar to the catheter tube 32.

The catheter tube 84 has a proximal portion, not shown, connectable with a manifold assembly 12 in substantially the same manner as is shown in FIG. 1. The catheter tube 84 defines an outer diameter of about 6 French throughout a substantial portion of its axial length, however, a reduced outer diameter portion 86 is located immediately adjacent the distal end 82 of the catheter tube 84. The reduced outer diameter portion 86 defines an outer diameter less than the outer diameter of the remainder of the catheter tube 84 by a length substantially equal to the thickness of the expandable member 80. Thus, an open end 88 of the expandable member 80 is fixedly attached by suitable means, such as an adhesive and the like, to the catheter tube 84 adjacent the reduced diameter portion 86 such that a substantially smooth outer surface profile is presented by the distal end 82.

The expandable member 80 is attached to the reduced portion 86 such that the reduced portion 86 extends into an interior of the expandable member 80. Thus, when the expandable member 80 is in a contracted condition, as is often the case when the energy treatment device 78 is inserted into the patient's body, the expandable member 80 can lie along or be wrapped down upon the reduced diameter portion 86 such that the distal end of the device 78 has a low profile for facilitating intravascular insertion and navigation of the energy treatment device 78.

The reduced portion 86 extends into the expandable member 80 a suitable distance for locating an electrode 89 within the interior of the expandable member 80. Specifically, the electrode 89 is disposed at a distal end 90 of the reduced portion 86 for delivering RF energy to the electrolyte fluid that passes through the fluid lumen 40, as discussed hereinabove. However, it is to be recognized that the electrode 89 differs from the electrode 38 in that the electrode 89 may include a number of apertures 92 therein for allowing passage of electrolyte fluid from the interior of the electrode 38 into the interior of the expandable member 80. These apertures 92, as will be discussed in greater detail later, allow for electrolyte fluid to be directed latitudinally with respect to the catheter tube 84 in addition to being directed longitudinally with respect to the catheter tube 84, as is provided by some of the prior art energy treatment devices. The apertures 92 can also provide an increased area for RF energy transmission from the electrode 89 to the electrolyte fluid. In addition, the electrode 89 can have any desirable configuration for performing certain treatment procedures.

The expandable member 80 may be constructed substantially similarly to a conventional angioplasty balloon, but, whereas an angioplasty balloon often has two fixed ends, the expandable member 80 has only one fixed, open end 88. The expandable member 80 is formed from an elastomeric material having sufficient memory properties so that the expandable member can have a predetermined shape, such as one which corresponds to the configuration of the particular tissues to be treated by the device 78, which the expandable member 80 assumes when it is expanded. The significance of this will become more clear later.

In the currently preferred embodiment of the energy treatment device 78, the expandable member 80 is formed from a polyolefin copolymer, such as Surlyn®, but may be formed from other materials, such as LATEX®. In the illustrated embodiment, the expandable member 80 assumes a shape having a substantially planar distal end 94, which may be particularly adept at forming a large area lesion on the tissues being treated without having to move the energy treatment device 78 with respect to the tissues. Thus, the expandable member 80 assumes a substantially pear-like shape, which may correspond to a configuration of tissues, such as those located within the coronary, within the patient's body. Of course, the expandable member 80 may be constructed to form any desired configuration upon expansion thereof.

During operation, electrolyte fluid flows through the fluid lumen 40 in the catheter tube 84 and into the interior of the expandable member 80 through the open, distal end 90 of the reduced portion 86 and/or the apertures 92 in the side of the electrode 89. The flow of electrolyte fluid into the interior of the expandable member 80 forces the expandable member 80 to move away from the outer surface of the reduced portion 86 of the catheter tube 84 to define the predetermined shape or configuration discussed above. As opposed to some angioplasty balloons, the expandable member 80 does not require a separate inflation lumen, or a compressed air source to deploy the expandable member 80. To facilitate transfer of RF energy from the electrode 89 to the tissues being treated, the expandable member 80 has a plurality of perforations 96 which allow electrolyte fluid to flow from the interior of the expandable member 80 to the tissues.

The structure of the energy treatment device 78 may become more clear upon reference to the following discussion of the operation thereof. Of course, this discussion of the operation of the device 78 is provided for illustrative purposes only and is not intended to limit the scope of this invention.

As the distal end of the energy treatment device 78 is inserted into the patient, the expandable member 80 is in the collapsed condition, overlying or being wrapped down on the reduced diameter portion 86, for facilitating intravascular insertion and navigation of the device 78 to the treatment site. The distal end 82 of the catheter tube 84 is positioned in proper orientation with respect to the tissues being treated, and the device 78 is activated, thereby energizing the electrode 89 with RF energy and causing electrolyte fluid to flow through the fluid lumen 40 towards the electrode 89 in substantially the same manner as discussed hereinabove.

The electrolyte fluid encounters the electrode 89 and picks up RF energy therefrom upon operative electrical contact with the electrode 89. Some of the electrolyte fluid flows through the electrode 89 and exits through the open, distal end 90 of the reduced portion 86, while some of the electrolyte fluid passes through the apertures 92 within the electrode 89. The electrode 89 is exposed to the electrolyte fluid as the fluid flows through the apertures 92, thereby effectively increasing the surface available for energy transmission from the electrode 89 to the electrolyte fluid. Also, the electrolyte fluid passing through the apertures 92 facilitates lateral deployment of the expandable member 80.

The RF energy-bearing electrolyte fluid leaves the electrode 89 and passes into the interior of the expandable member 80. The presence and force of flow of the electrolyte fluid causes the expandable member 80 to move from the contracted condition into the expanded condition illustrated in FIG. 5. When sufficient electrolyte fluid has flowed into the interior of the expandable member 80, the member 80 assumes its preformed configuration, which preferably corresponds to the configuration of the tissues being treated by the energy treatment device 78. The preformed configuration allows the perforations 96 in the expandable member 80 to positively direct RF energy-bearing electrolyte fluid towards the tissues that need to be treated with RF energy.

The energy-bearing electrolyte fluid passes from the interior of the expandable member 80 towards the tissues to be treated through the perforations 96. The placement of the perforations 96 on the expandable member 80 can also be predetermined for directing flow of electrolyte fluid towards selected sites on the tissues. In addition, the expandable member 80 can be variably expanded to define various configurations for positively directing energy-bearing electrolyte fluid against tissues to be treated while using a single device. Thus, in this manner, the energy treatment device 78 allows for selective energy treatment of predetermined tissues, and for tailoring the energy treatment to particular tissue configurations within a patient's body.

After the tissues have been sufficiently treated, the flow of electrolyte fluid through the energy treatment device 78 is stopped, and the electrode 89 is no longer energized with RF energy. Because electrolyte fluid is no longer flowing into the interior of the expandable member 80, the elastomeric nature of the material comprising the member 80 causes it to return towards the original, contracted condition. The distal end of the energy treatment device 78 can now be relatively easily moved within or removed from the patient's body because the expandable member 80 again defines a low profile.

Yet another embodiment of the invention, an electrophysiology treatment device 98, is illustrated in FIG. 6. The treatment device 98 is substantially similar to the treatment device 10, except for the differences to be noted herein, hence the like reference numerals for similar structures. Specifically, the treatment device 98 includes an additional novel construction of the means for positively directing electrolyte fluid flow towards tissues to be treated with electrical energy. This novel construction of the means takes the form of a deflecting body 100 which is configured for deflecting energy-bearing electrolyte fluid in a certain, predetermined flow path, which can be configured to correspond to the configuration of the tissues to be treated.

The wire 22 extends through the wire lumen 30 in substantially the same fashion as described earlier, and the distal end 48 of the wire 22 is electrically connected to a proximal end of an electrode 102 by a bead 50 of solder and the like. A proximal end 104 of the deflecting body 100 is attached to a distal end of the electrode 102 by an adhesive 106, preferably an epoxy, such that the deflecting body 100 extends distally from the electrode 102.

Because the electrode 102, in the illustrated embodiment, has to support the deflecting body 100, the electrode 102 is preferably in the form of a solid cylinder for insuring a firm connection between the electrode 102 and the deflecting body 100, and also to provide the deflecting body 100 with secure attachment to the remainder of the energy treatment device 98 so that the deflecting body 100 is not appreciably moved by electrolyte fluid flowing around the deflecting body 100. Of course, other configurations for the electrode 102 are also possible without departing from the scope of the present invention.

In order to provide additional support to the deflecting body 100, the electrode 102, and the wire lumen 30, at least one spline 108 is provided extending radially inwardly from an inner diameter surface of the catheter tube 32. The spline 108, in the illustrated embodiment, engages the outer diameter surface of the wire lumen 30, thereby supporting the wire lumen 30, and thus the deflecting body 100, and maintaining those structures substantially concentrically disposed with respect to the catheter tube 32. This insures that the desired deflection or dispersion of energy-bearing electrolyte fluid occurs.

The deflecting body 100 itself, in the illustrated embodiment, has a substantially frusto-conical shape with a flared or enlarged portion 110 thereof extending beyond a distal end 112 of the catheter tube 32. The deflecting body 100 is preferably constructed from a non-conductive material, such as TEFLON® and the like, so that electrical energy is not transferred from the electrode 102 or the electrolyte fluid to the deflecting member 100. Thus, the deflecting body 100 can reside within the electrolyte fluid flow path without absorbing electrical energy from the electrolyte fluid. In addition, it is to be noted that the deflecting body 100 may have a configuration different from the configuration illustrated in FIG. 6 without departing from the scope of the invention. The configuration of the deflecting body 100 may be of any desired shape, and can have a configuration which corresponds to a configuration of tissues to be treated by the energy treatment device 98. Thus, the configuration of the deflecting body 100 can be predetermined for positively directing energy-bearing electrolyte fluid to desired, selected areas on the patient's tissues.

One specific employment of the deflecting body 100 is to shield areas of the tissues being treated from at least some of the electrolyte fluid, thereby providing for selective treatment of the tissues. This specific employment will be discussed in detail because it may give the reader greater appreciation for the novel aspects of the embodiments of the invention, however, it is to be fully understood that this detailed discussion is provided for illustrative purposes only, and is not intended to limit the scope of the invention.

As shown in FIG. 6, when energy-bearing electrolyte fluid encounters the deflecting body 100 as it passes through the distal end of the catheter tube 32, interference between the electrolyte fluid and the deflecting body 100 causes the path of fluid flow to be positively directed or deflected responsive to the configuration of the deflecting body 100. Thus, while the path of fluid flow, indicated by arrows 54, within the catheter tube 32 may be relatively focused, once the electrolyte fluid encounters the deflecting body 100, the path of fluid flow, indicated by arrows 114, as the electrolyte fluid passes the distal end 112 of the catheter tube 32 spreads out, or disperses. Because of this difference in concentration of fluid flow, different lesions can be formed on the tissues being treated, and various portions of the tissues may be shielded from the heating effects of the energy-bearing electrolyte fluid.

As shown in FIG. 7, a relatively concentrated or substantially focused fluid flow path, indicated by arrows 54, encounters and transfers electrical energy to tissues 116 being treated. This focused fluid flow path 54 can be produced, for example, by the energy treatment devices 10 and 66. Because the flow path 54 of electrolyte fluid is relatively concentrated, a focused lesion is formed, represented by the necrotic zone 118 of heated or treated tissue cells. Also, the concentrated fluid flow can produce a crater 120 on the tissues 116 at the location of most direct contact between the energy-bearing electrolyte fluid and the tissues 116. Production of the crater 120 requires a significant amount of energy to be transferred to a small area on the tissues, which limits the dimensions of the necrotic zone 118 by a corresponding amount. In this manner, a focal lesion may be formed.

In contrast, FIG. 8 depicts a relatively dispersed fluid flow path, indicated by arrows 114, encountering a similar portion of tissues 116. This fluid flow path can be produced by the energy treatment devices 56, 78 and 98. Because the fluid flow path 114 is not as focused as the fluid flow path 54 shown in FIG. 7, no crater 120 is formed on the tissues 116. Instead, the energy in the energy-bearing electrolyte fluid is transferred to a relatively larger portion of the tissues 116, thereby forming a necrotic zone 122 having dimensions larger than those of the necrotic zone 118. The necrotic zone 122 may have achieved deeper penetration into the tissues 116 because electrical energy is not expended in forming the crater 120. In this manner, a large area lesion may be formed.

Upon comparison of the necrotic zones 118 and 122, some of the benefits provided by the embodiments of the present invention may become clear. The energy treatment device 10, 56, 78 or 98 may be used to produce either focal lesions or large area lesions. Any desired configuration or depth of lesions may be produced by the energy treatment devices 10, 56, 78 or 98 by suitable construction of the means for positively directing flow of energy-bearing electrolyte fluid. This novel means allows a treating physician to tailor delivery of energy-bearing electrolyte fluid for different tissues without having to move the treatment device 10, 56, 78 or 98 with respect to those tissues. The treatment devices 10, 56, 78 or 98 provide for shielding of desired tissues from energy treatment. The lesions producible by the embodiments of the invention are almost limitless, which may provide treating physicians with greater flexibility in performing electrophysiology treatments. Also, electrophysiology treatments may be provided with expanded indications of use, and may be employable in vasculature other than the coronary, such as the peripheral vasculature.

The various embodiments and methods of the invention present numerous improvements and advances in the field of treating tissues within a patient's body with electrical energy, and specifically with RF energy. These devices and methods contribute significantly to the art of electrophysiology ablation or tissue treatment. One novel aspect of the present embodiments is that these embodiments utilize a novel method of conduction of energy, viz. an electrolyte fluid, from a source 20 of such energy to the tissues within the patient being treated. This aspect allows the energy treatment devices 10, 56, 66, 78 and 98 to deliver treating energy to the tissues without having to be maintained in physical contact with those tissues during the treatment procedure. This is a significant improvement over some of the electrophysiology ablation or tissue treatment devices of the prior art which require maintenance of physical engagement with the tissues to be treated.

The energy treatment devices 10, 56, 66, 78 and 98 of the invention are able to deliver energy to a tissue area within the patient's body which is larger than a corresponding area of some prior art devices. Furthermore, the embodiments and methods of the invention allow the energy treatment devices 10, 56, 66, 78 and 98 to deliver energy to a positively variably sized tissue area within a patient. In addition, heat does not build up in the distal, in-body ends of the energy treatment devices 10, 56, 66, 78 and 98 of the invention during operation thereof as significantly as it does in some of the prior art electrophysiology devices. Also, the distal tips of the energy treatment devices 10, 56, 66, 78 and 98 are substantially non-thrombogenic, thereby increasing the efficiency of these devices.

While preferred embodiments of the present invention are shown and described, it is envisioned that those skilled in the art may devise various modifications of the present invention without departing from the spirit and scope of the appended claims.

We claim:

1. An apparatus for ablating body tissue using radio frequency (RF) energy, comprising:
   a catheter having a proximal portion attachable to a source of electrolyte fluid, a distal portion sized for insertion into a patient's body, and a lumen for delivering fluid from the proximal portion to the distal portion;
   an expandable member disposed on the distal portion of the catheter and comprising a substantially planar distal end, the expandable member defining an interior region in communication with the lumen; and
   an RF electrode on the distal portion and communicating with the lumen, the electrode configured for coupling to a source of RF energy, whereby RF energy may be transferred from the electrode to selected tissue areas in a patient's body via electrolyte fluid delivered through the lumen and into the interior region of the expandable member, the electrode extends from the distal portion of the catheter, the electrode comprising an interior communicating with the lumen.

2. The apparatus of claim 1, wherein the expandable member is attached to the distal portion such that a substantially smooth outer surface profile is presented by the distal portion.

3. The apparatus of claim 1, wherein the distal portion extends into an interior space of the expandable member.

4. The apparatus of claim 1, wherein the expandable member defines an interior space in communication with the lumen and wherein the electrode is disposed within the interior space.

5. The apparatus of claim 4, wherein the electrode comprises a plurality of apertures, the apertures allowing electrolyte fluid to pass therethrough into the interior space.

6. The apparatus of claim 1, wherein the expandable member further comprises a plurality of perforations to allow flow of electrolyte fluid from an interior space of the expandable member to the selected tissue areas beyond the expandable member.

7. The apparatus of claim 1, wherein the catheter is flexible.

8. An apparatus for ablating body tissue using radio frequency (RF) energy, comprising:
   a source of RF energy;
   a catheter having a proximal portion attachable to a source of electrolyte fluid, a distal portion sized for insertion into a patient's body, and a lumen for delivering fluid from the proximal portion to the distal portion;
   a porous member attached to the distal portion of the catheter, the porous member defining an interior region in communication with the lumen, the interior region capable of receiving electrolyte fluid delivered from the proximal portion of the catheter; and
   an electrode disposed in the interior region and coupled to the source of RF energy the electrode extends from the distal portion of the catheter.

9. The apparatus of claim 8, wherein the porous member has a substantially planar distal end.

10. The apparatus of claim 8, wherein the catheter is flexible.

* * * * *